US012661475B2

(12) United States Patent
Anderson et al.

(10) Patent No.: US 12,661,475 B2
(45) Date of Patent: Jun. 23, 2026

(54) OXYGEN LINE VERIFICATION FOR ANESTHESIA GAS FLOW CONTROLS

(71) Applicant: Hu-Friedy Mfg. Co., LLC, Chicago, IL (US)

(72) Inventors: Steve R. Anderson, Mesa, AZ (US); Thomas Strele, Phoenix, AZ (US); E. Daniel Shoemaker, Phoenix, AZ (US)

(73) Assignee: HU-FRIEDY MFG. CO., LLC, Chicago, IL (US)

( * ) Notice: Subject to any disclaimer, the term of this patent is extended or adjusted under 35 U.S.C. 154(b) by 852 days.

(21) Appl. No.: 17/999,418

(22) PCT Filed: May 27, 2021

(86) PCT No.: PCT/US2021/034397
§ 371 (c)(1),
(2) Date: Nov. 21, 2022

(87) PCT Pub. No.: WO2021/252196
PCT Pub. Date: Dec. 16, 2021

(65) Prior Publication Data
US 2023/0201511 A1     Jun. 29, 2023

Related U.S. Application Data

(60) Provisional application No. 63/037,654, filed on Jun. 11, 2020.

(51) Int. Cl.
*A61M 16/10*     (2006.01)
*A61M 16/00*     (2006.01)
(Continued)

(52) U.S. Cl.
CPC ...... *A61M 16/1005* (2014.02); *A61M 16/024* (2017.08); *G01N 9/266* (2013.01);
(Continued)

(58) Field of Classification Search
CPC ............ A61M 2205/276; A61M 16/12; A61M 2016/0027; A61M 16/024;
(Continued)

(56) References Cited

U.S. PATENT DOCUMENTS 4,552,164 A     11/1985   Urella
4,572,000 A     2/1986    Kooiman
(Continued)

FOREIGN PATENT DOCUMENTS

CA     2499147     3/2004
EP     0658759 B1   5/2000
(Continued)

OTHER PUBLICATIONS

International Preliminary Report on Patentability issued in PCT/US2021/034397, mailed Dec. 22, 2022.
(Continued)

*Primary Examiner* — Bradley H Philips
*Assistant Examiner* — Abigayle Dale
(74) *Attorney, Agent, or Firm* — MARSHALL, GERSTEIN & BORUN LLP

(57)     ABSTRACT
Various examples disclosed relate to an apparatus and method for use in verifying input gas, such as differences between a first and a second gas in an anesthesia flow control where one of the gases is oxygen gas and the other of the gases is nitrous oxide gas. The apparatus can include, for example, a chamber having an inlet to receive gas and a vent to exhaust the gas, a gas control to fill the chamber with the gases to a determined begin pressure, and a microprocessor configured to measure respective times to exhaust the first gas and the second gas from the chamber, via the vent, to reach a determined end pressure. Based on time to exhaust the respective gases, a difference between the first and second gases can be identified; this verification can verify
(Continued)

that improper crossover/cross-connection of gas supply lines is not present.

18 Claims, 6 Drawing Sheets

(51) Int. Cl.
  *G01N 9/26*          (2006.01)
  *G01N 11/06*          (2006.01)

(52) U.S. Cl.
  CPC ..... *G01N 11/06* (2013.01); *A61M 2016/0027* (2013.01); *A61M 2016/003* (2013.01); *A61M 2202/0208* (2013.01); *A61M 2202/0283* (2013.01)

(58) Field of Classification Search
  CPC ........ A61M 16/1005; A61M 2016/003; A61M 16/201; A61M 16/0051; A61M 16/01; A61M 16/104; A61M 2202/0007; A61M 16/085; A61M 16/10; A61M 2202/0208; A61M 2202/0283; G01N 11/02; G01N 11/04; G01N 11/06; G01N 11/08; G01N 9/26; G01N 9/266
  See application file for complete search history.

(56)                References Cited

U.S. PATENT DOCUMENTS

| | | | |
|---|---|---|---|
| 4,627,271 | A | 12/1986 | Abbott et al. |
| 4,784,486 | A | 11/1988 | Van Wagenen et al. |
| 4,890,482 | A | 1/1990 | Maini |
| 4,934,178 | A * | 6/1990 | Jones ..................... G01N 9/266 73/32 R |
| 6,076,392 | A * | 6/2000 | Drzewiecki ........... G01F 1/3227 73/23.3 |
| 6,286,360 | B1 | 9/2001 | Drzewiecki |
| 6,857,443 | B2 | 2/2005 | Volgyesi |
| 9,086,313 | B2 | 7/2015 | Tobia et al. |
| 10,974,006 | B2 | 4/2021 | Sundling |
| 2006/0196505 | A1* | 9/2006 | Izuchukwu ......... A61M 16/104 128/203.15 |
| 2008/0078389 | A1* | 4/2008 | Xiao ..................... A61M 16/12 128/204.22 |
| 2015/0034085 | A1* | 2/2015 | Klein .................. A61M 16/026 128/203.14 |
| 2015/0320953 | A1* | 11/2015 | Acker ................... A61M 16/12 128/203.14 |
| 2016/0310918 | A1 | 10/2016 | Baldus |
| 2017/0100553 | A1 | 4/2017 | Ahearn et al. |
| 2018/0339279 | A1 | 11/2018 | Baldus |

FOREIGN PATENT DOCUMENTS

| | | | |
|---|---|---|---|
| EP | 2480277 A1 | 8/2012 | |
| EP | 2492666 B1 | 6/2019 | |
| GB | 2041225 A * | 9/1980 | .......... A61M 16/104 |

OTHER PUBLICATIONS

International Search Report and Written Opinion of International Patent Application No. PCT/US21/34397 filed May 27, 2021, mailed Oct. 12, 2021.

* cited by examiner

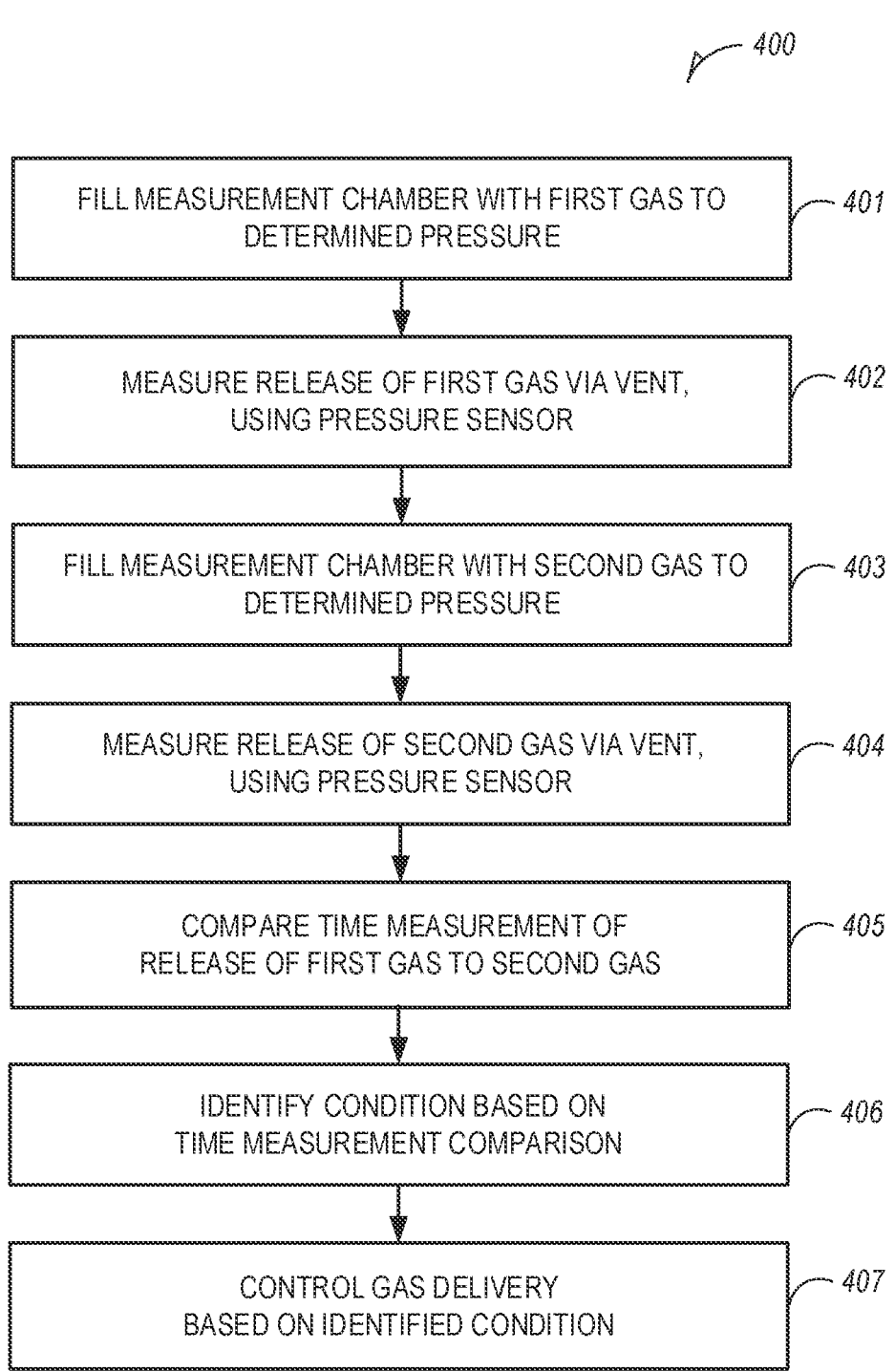

*400*

| FILL MEASUREMENT CHAMBER WITH FIRST GAS TO DETERMINED PRESSURE | *401* |

| MEASURE RELEASE OF FIRST GAS VIA VENT, USING PRESSURE SENSOR | *402* |

| FILL MEASUREMENT CHAMBER WITH SECOND GAS TO DETERMINED PRESSURE | *403* |

| MEASURE RELEASE OF SECOND GAS VIA VENT, USING PRESSURE SENSOR | *404* |

| COMPARE TIME MEASUREMENT OF RELEASE OF FIRST GAS TO SECOND GAS | *405* |

| IDENTIFY CONDITION BASED ON TIME MEASUREMENT COMPARISON | *406* |

| CONTROL GAS DELIVERY BASED ON IDENTIFIED CONDITION | *407* |

*FIG. 4*

OXYGEN LINE VERIFICATION FOR ANESTHESIA GAS FLOW CONTROLS

PRIORITY CLAIM

This application claims priority to and the benefit of U.S. Provisional application with Ser. No. 63/037,654, filed on Jun. 11, 2020, entitled OXYGEN LINE VERIFICATION FOR ANESTHESIA GAS FLOW CONTROLS, which is herein incorporated by reference in its entirety.

BACKGROUND

Nitrous oxide ($N_2O$) and oxygen ($O_2$) are used for anxiety relief, pain relief and anesthesia in a variety of dental and medical procedures. These gases are commonly delivered by a gas flow meter ("flowmeter" or "mixer") which accepts $O_2$ and $N_2O$ gas from outside sources, mixes the gases according to the direction of the anesthesia operator, and then delivers the mixed gases to the patient.

One risk to patients with this form of anesthesia occurs if the oxygen flow is too low, or the flow of nitrous oxide is too high, as either can lead to oxygen deprivation. The primary cause of oxygen deprivation in nitrous oxide anesthesia settings occurs due to an improper crossover/cross-connection of supply lines, where the flowmeter receives nitrous oxide or some other non-oxygen gas into its oxygen intake. The flowmeter treats this gas as if it was oxygen, which may lead an anesthesia operator to deliver 100% nitrous oxide even though the operator may intend to deliver 100% $O_2$. Unfortunately, this outcome has not been eliminated by current types of safety precautions and devices, leading to serious injuries and sometimes deaths of patients.

This dangerous outcome may be caused by building gas supply pipes not being installed correctly and not verified by a safety inspector, improper fittings being installed on the gas supply hoses, or other erroneous events. For instance, different and incompatible gas fittings are designed for use with oxygen and nitrous oxide supply lines and inlets to identify (and restrict) the different sources of gas. However, this measure fails if a user mistakenly installs an oxygen fitting onto a nitrous oxide supply hose, which can cause the nitrous oxide line to be connected into an oxygen inlet of a flowmeter. Likewise, many anesthesia flowmeters that are designed for use with nitrous oxide include an oxygen "failsafe" component usable with the flowmeter to stop the flow of nitrous oxide if oxygen gas is not flowing. However, this failsafe component simply measures the presence of gas pressure or flow in the oxygen line, and the failsafe component cannot tell if the gas that is being measured is actually oxygen. Thus, if the lines are crossed prior to entering the failsafe, the flowmeter will operate as if it is delivering pure oxygen, when the flowmeter is actually delivering nitrous oxide or another non-oxygen gas.

SUMMARY

Disclosed herein is an apparatus and associated methods for analyzing the characteristics of a gas being delivered via a gas line, configured for distinguishing between oxygen and nitrous gas lines or other situations where delivery of multiple gases is involved. The analysis of the gas may include the use of a sampling technique to perform a measurement of a controlled leak under pressure from a designated chamber. The technique can include the observation and comparison of leak times for a first gas (e.g., nitrous oxide) and a second gas (e.g., oxygen) from this chamber. Because the density of oxygen gas (~1.429 g/ℓ) and the density of nitrous oxide gas (~1.977 g/ℓ) cause different leak rates, the sampling technique can be used to confirm that the first gas has a density that is different than the second gas, and thus identify a difference between the first gas and the second gas. Based on the identification of this difference, a comparison of oxygen gas versus nitrous oxide gas can be performed, such as to verify that oxygen gas is being received from an intake designated to receive the oxygen gas, and to verify that nitrous oxide gas is being received from an intake designated to receive the nitrous oxide gas.

In an example, this sampling technique may be integrated as a safety component or function, and embodied within a standalone gas analysis device, a flowmeter component, an oxygen failsafe component, a manifold component, or other form of sensing or control apparatus used with gas mixing, delivery, or supply. The identification of an abnormal or unexpected (unsafe) condition may be used to cause a system shutdown, a change in gas mixture, a disconnection, an output alert or indication, or other precautionary or evasive action. Likewise, the identification of a normal or expected (safe) condition may be required as a precondition for the operation of a flowmeter, or used before the mixing or output of one or both gases or for other gas control operations.

In an example, an apparatus for verifying input gases may include a configuration including: a chamber (or separate chambers) adapted to receive a gas, the chamber including an inlet to receive the gas and a vent to exhaust the gas; a pressure sensor arranged to measure pressure within the chamber(s); a gas control coupled to the inlet, which fills a first gas and a second gas into the chamber(s) at respective times (or at the same time with separate chambers); and microprocessor circuitry to operate logic to measure and respond to the measurement of leak times. For instance, this logic may include observing pressure in the chamber at a first time period to identify a first elapsed time to exhaust the first gas from the chamber and reach a defined end pressure; observing pressure in the chamber at a second time period to identify a second elapsed time to exhaust the second gas from the chamber and reach the defined end pressure; and identifying a difference between the first gas and the second gas, based on a time difference between the first elapsed time and the second elapsed time. Various controls, signals, or identifications may be caused based on a difference between the elapsed time to reach the defined end pressure from gas received at an intake designated to receive nitrous oxide gas, and the elapsed time to reach the defined end pressure from gas received at an intake designated to receive oxygen gas.

In an example, a gas flow control system, including components for verifying input gases, may include a configuration including: a first intake adapted to receive a first gas and a second intake adapted to receive a second gas, where one of the first and second intake is designated to receive oxygen gas, and the other of the first and second intake is designated to receive nitrous oxide gas; a chamber (or multiple chambers) including an inlet to receive gas and a vent to exhaust the gas; and a gas control operable to respectively fill the chamber with the first gas and fill the chamber with the second gas to a determined begin pressure; and a microprocessor configured to measure respective times to exhaust the first gas and the second gas from the chamber, via the vent, and reach a determined end pressure. In this configuration, the microprocessor operates the gas control to enable gas flow for the first gas and the second gas, for output with mechanical or digital a gas flow meter, if a time to exhaust a gas received from the intake designated to receive the nitrous oxide gas exceeds the time to exhaust a gas received from the intake designated to receive the oxygen gas.

In an example, a method of verifying input gases may be performed by an apparatus, component, system, or other entities described herein. The method of verifying the input gases may include: filling a chamber with a first gas to a defined begin pressure (e.g., 35 to 45 psi gauge); monitoring pressure in the chamber during the first time period, using a pressure sensor, to measure a first time to exhaust the first gas from the chamber, via a vent (e.g., a fixed orifice, such as a pinhole), to reach a defined end pressure (e.g., 5 to 10 psi gauge); filling the chamber with a second gas to the defined begin pressure; monitoring pressure in the chamber during the second time period, using the pressure sensor, to measure a second time to exhaust the second gas from the chamber, via the vent, to reach the defined end pressure; and identifying a difference between the first and second gas, based on a difference between the first time and the second time. For instance, this method may verify one of the first and second gases as oxygen, and the other of the first and second gases as nitrous oxide, if the time to reach the defined end pressure by exhaust of the nitrous oxide gas exceeds the time to reach the defined end pressure by exhaust of the oxygen gas.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 4 includes a flowchart depicting a method of verifying and controlling gas delivery for anesthesia gases, according to an example.

DETAILED DESCRIPTION

Figure 1:
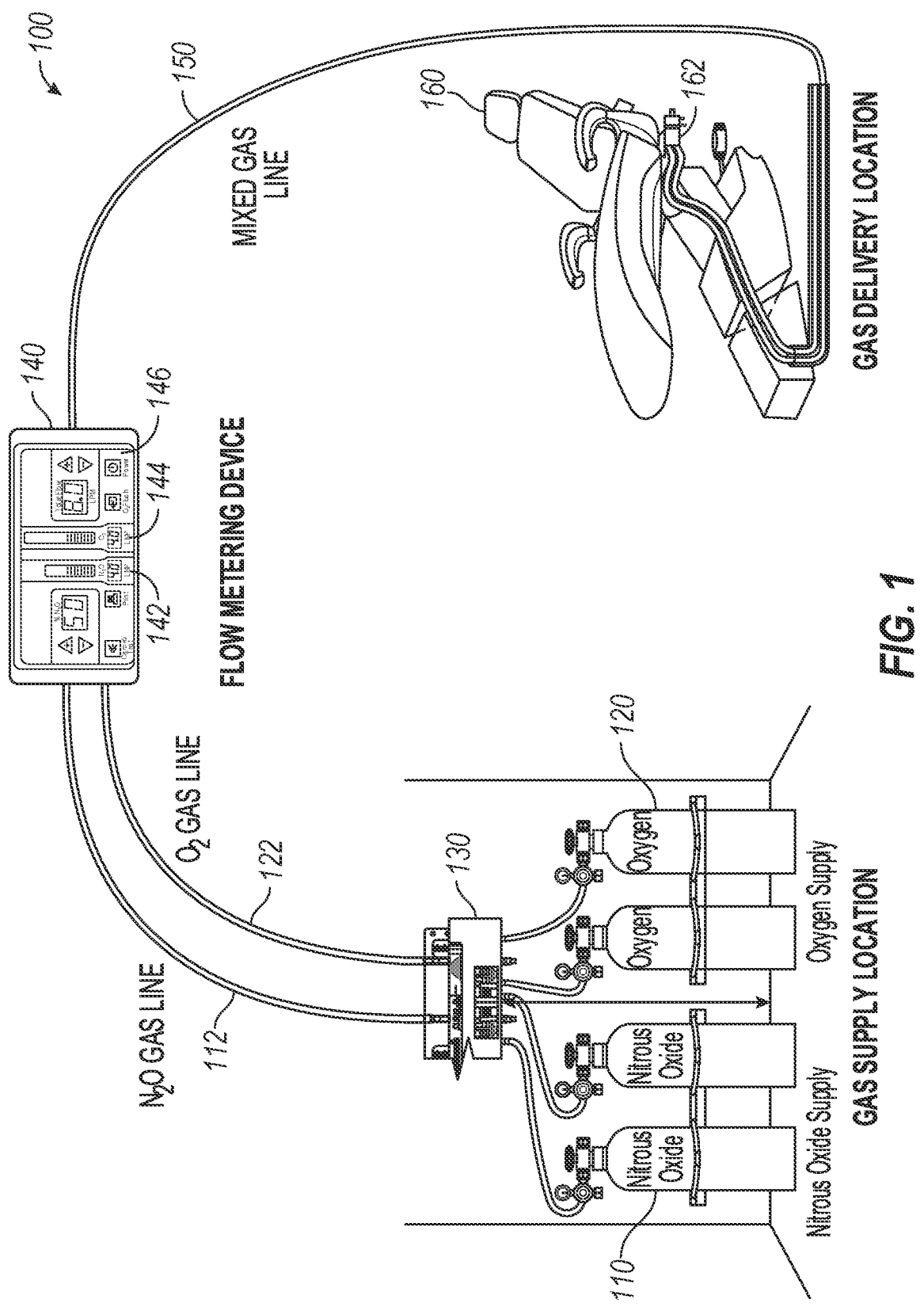
FIG. 1 illustrates an operational scenario using gas flow control equipment for delivery of anesthesia gases, according to an example.

The present disclosure describes, among other aspects, devices and methods for identifying properties of and differentiating between gases used in anesthesia gas control equipment. In particular, the following describes a detection system and method used to distinguish between oxygen and nitrous oxide gases with use of a measured exhaust procedure. This procedure can involve, among other operations, the observation of gas pressure within a chamber, and the measurement of time for a first and a second gas to leak from the chamber. Gases with lower density—such as oxygen— will leak faster than heavier gases such as nitrous oxide. Based on the difference in time for the first and the second gas to be exhausted from the chamber (e.g., with a consistent exhaust vent and a chamber pressure measurement(s)), differences in density between the first gas and the second gas can be identified. In a similar procedure, based on a comparison of the time to exhaust a particular gas to an expected time, ratio of times, or other measurement to exhaust the particular gas, the properties of a single gas can be identified as within—or outside of—an expected operational range.

The disclosed detection system and method can enable a verification of the gas provided from inlets associated with the first gas and the second gas, or the verification of properties of one gas or multiple gases, for a variety of safety and operational purposes. For instance, a verification procedure may identify that gas flowing through an inlet designated for oxygen is correctly oxygen gas, and gas flowing through an inlet designated for nitrous oxide is correctly nitrous oxide gas, due to the heavier density of nitrous oxide which causes it to take more time to exhaust from the vent relative to oxygen. The verification procedure may also identify scenarios in which an incorrect gas (or an unknown gas or gas mixture) is provided in contravention of expected gas properties.

In the context of existing anesthesia gas control equipment such as digital flowmeters, one function of the gas control equipment is to provide accurate controls that deliver combined gas (a mixture of $O_2$ and $N_2O$) as an output at a fixed flow rate, allowing an output mixture to provide a precise percentage of a gas composition. Such gas control equipment can monitor for gas flow rate, to ensure that a connected gas source can provide gas, and specifically in the case of oxygen to ensure that a source of oxygen gas appears available for at least emergency purposes. However, within such gas control equipment, there is currently no way to know if the oxygen and nitrous oxide gas input lines are accidentally reversed, if the oxygen and nitrous oxide gas input lines are connected to the same type of gas, or if oxygen gas is missing entirely. In any of these scenarios, the flow of gas may appear normal even as the wrong gas is selected to be delivered, leading to unforeseen consequences.

Although oxygen sensors which use chemical reagents can detect the presence of oxygen gas, the use of such sensors has not been widely implemented in anesthesia gas control settings to identify or prevent reversed gas lines and other dangerous operational faults. Existing failsafe and safety devices cannot ensure that a source of oxygen, needed for emergency settings, is actually available for patient use. These and other safety and technical limitations are addressed by the following systems and methods.

FIG. 1 illustrates an operational scenario 100 using gas flow control equipment for delivery of anesthesia gases. The operational scenario 100 specifically focuses on the delivery of anesthesia gases from a gas supply location to a gas delivery location, as mixed and controlled via a flow metering device 140. Although this operational scenario 100 is suggestive of a gas supply and delivery scenario via built-in (e.g., centralized, permanently installed) components of a medical facility, it will be understood that the gas supply and delivery scenario may also apply to portable or movable components. For instance, the flow metering device 140 may be integrated with gas supply equipment on a cart, to enable movement among different patient rooms or locations. It will be understood that the arrangement and components in the operational scenario 100 is provided for purposes of illustration and not necessarily limitation. Also, as discussed herein, usage of the term "anesthesia" is intended to be interchangeable with the terms "analgesia" and "conscious sedation", to encompass multiple forms of medically-induced pain control using nitrous oxide.

Within the operational scenario 100, anesthesia gases such as nitrous oxide gas and oxygen gas are sourced from a nitrous oxide supply 110 and an oxygen supply 120 at a gas supply location. For example, the gas supply location may supply one or multiple delivery locations in a medical facility with the anesthesia gases, from among one or multiple supply tanks. In an example, the nitrous oxide supply 110 and the oxygen supply 120 are connected to a gas manifold 130 which enables distribution of gases within the medical facility. The manifold 130 may include various gas flow control and monitoring capabilities to enable uninterrupted or monitored distribution of the respective gases to one or multiple delivery locations, such as with automatic gas cylinder changeover, verification of line pressure, and the like.

The output from the manifold 130 includes two gas lines, specifically a nitrous oxide gas line 112 and an oxygen gas line 122, which deliver gas to the flow metering device 140. The flow metering device 140 enables mixing of the anesthesia gases delivered from the gas lines 112, 122, according to gas mixtures being specified by input controls of the flow metering device 140. In an example, the flow metering device 140 includes a user control 146 with various input controls (e.g., buttons, knobs, input screens, etc.) and output indicators (e.g., LED/LCD display components, digital indicators, output screens, etc.) relating to the mixture and delivery of the anesthesia gas. In other examples, the flow metering device 140 is operably connected to other electronic or computing devices (e.g., personal computers, workstations, mobile devices, etc.) for control, monitoring, or logging purposes. In other examples, the flow controls of the flow metering device 140 are strictly mechanical and the flow indicators are ball and tubes.

In an example, the flow metering device 140 can include an output indication 142 for an output status of the nitrous oxide gas and an output indication 144 for an output status of the oxygen gas, which are mixed into a gas mixture provided via a mixed gas line 150. This mixed gas line 150 may provide delivery of the gas to a gas delivery location 160 (such as a dentist office chair or medical facility procedure location), including from a chairside terminal 162. Further delivery of the gases from the mixed gas line 150 and the chairside terminal 162 to a patient are not shown in FIG. 1. However, it will be understood that additional gas delivery hoses, vacuum hoses, a gas delivery masks, and other features or components may be involved for safe administration of the mixed anesthesia gases to a particular patient.

Figure 2:
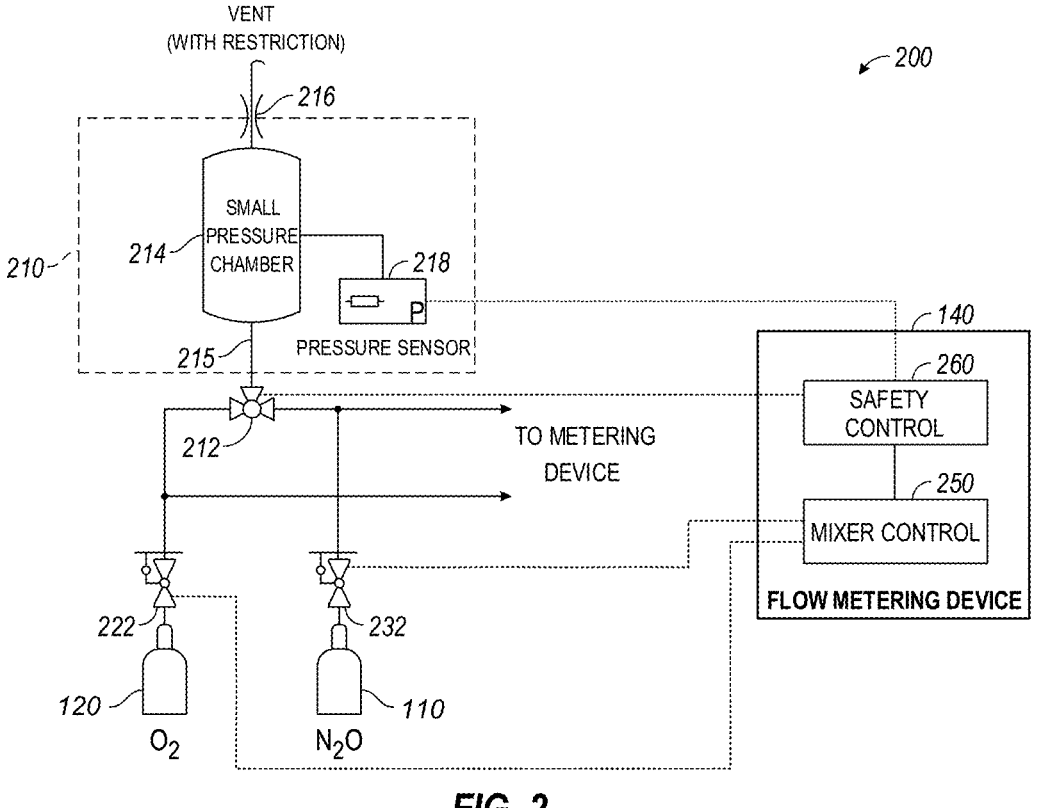
FIG. 2 illustrates a schematic diagram of an anesthesia gas verification arrangement, according to an example.

FIG. 2 illustrates a schematic diagram of an anesthesia gas verification arrangement 200, based on a configuration of a gas verification apparatus 210. In various examples, the gas verification apparatus 210 may be a standalone device or integrated into a gas control system such as a flowmeter apparatus or system. For purposes of illustration, the gas verification apparatus 210 is illustrated as separate from the control components of the flow metering device 140 but connected to a same gas supply line. In other configurations, the gas verification apparatus 210 can be integrated with the flow metering device 140.

In an example, the gas verification apparatus 210 may be integrated within a flow mixing or metering system, including being located within a housing for a flowmeter. In a varying example, the gas verification apparatus 210 may be external to the housing of a flowmeter. For instance, the gas verification apparatus 210 may be integrated with an oxygen failsafe device (not shown), which operates to supply oxygen or restrict non-oxygen gases in the case of a low pressure or flow of oxygen. In a varying example, the gas verification apparatus 210 may be integrated into a gas switching, mixing, or control apparatus, such as the manifold 130, or other centralized or installed equipment. In the following example, the gas verification apparatus 210 is referenced as being located within or operably coupled to a flow metering device 140, such as being controlled by a safety control 260 within the flow metering device.

The gas verification apparatus 210 is illustrated as including a pressure chamber 214, which includes an inlet 215 to receive gas, and a vent 216 to exhaust gas. The gas verification apparatus 210 further includes a pressure sensor 218 adapted to measure the pressure of gas within the chamber 214. A sequence of chamber pressure and time measurements for each measured gas may be performed as discussed below. In an example, the gas verification apparatus 210 may include a microprocessor (not shown) used to control the chamber pressure and perform the time measurements; in other examples, the safety control 260 or other components of the flow metering device 140 may include a microprocessor to control the chamber pressure and perform the time measurements.

The gas supply arrangement depicted in FIG. 2 provides a further use of the oxygen and nitrous oxide gas supply depicted in operational scenario 100; however, it will be understood that the gas supply arrangement depicted in FIG. 2 may be arranged for other operational scenarios. The gas supply arrangement in FIG. 2 specifically includes the supply of an oxygen gas 120 controlled by a reducing valve 222, and the supply of a nitrous oxide gas 110 controlled by a reducing valve 232. The supplies of these gases 110, 120 is provided to the flow metering device 140 with additional gas connections, valves, actuators, and sensors not shown in detail in FIG. 2. The operation of the reducing valves 222, 232 are respectively controlled by a mixer control 250 of the flow metering device 140, which operates as a gas mixer.

In an example, the supplies of the nitrous oxide gas 110 and the oxygen gas 120 are provided to the gas verification apparatus 210 through the use of a three-way valve 212. In an example, the control of the three-way valve 212 is provided from a safety control 260 integrated within the flow metering device 140. For instance, the safety control 260 may control the dispensing of the respective gases into the chamber 214, based on monitoring of the pressure in the chamber 214 as indicated by the pressure sensor 218. The safety control 260 may include a microprocessor or other processing circuitry used to measure the chamber pressure, and perform an evaluation of a time for the respective gases to exhaust from a begin pressure to an end pressure (e.g., the amount of time for the gas to exhaust from 40 psi to 5 psi (pounds-per-square-inch) gauge (relative to atmospheric pressure)). With this measurement, the safety control 260 may verify that a gas, provided from a supply line designated (e.g., labeled, fitted) to provide oxygen, exhausts from the vent 216 of the chamber 214 more quickly than a gas provided from a supply line designated to provide nitrous oxide. The safety control 260 may perform other types of comparisons or measurements.

In various examples, a microprocessor or other processing circuitry (not shown) may be integrated within the gas verification apparatus 210 to perform pressure readings of the chamber from the pressure sensor 218 and associated time measurements or comparisons. For example, the safety control 260 may be operably coupled to such circuitry and receive an indication that a time comparison between the first gas and second gas exceeds a defined threshold, is within a defined range, matches a particular ratio or ratio range, etc.

The gas verification apparatus 210 can perform a sequence to fill the pressure chamber 214 with each gas to at least a defined or calculated begin pressure and exhaust the pressure chamber 214 with each gas to at least a defined or calculated end pressure. A microprocessor may operate a timer that starts and stops based on pressure sensor measurements of the begin and end pressure, respectively. The amount of time needed to fill a gas in the pressure chamber 214 to the defined begin pressure and exhaust the gas in the pressure chamber 214 to the defined end pressure may be on the manner of tenths of seconds or seconds; for instance, each fill and exhaust cycle may be designed to take from about 0.3 seconds to about 0.5 seconds, depending on the size of the pressure chamber 214 and the vent 216. Thus, the operation of the gas verification apparatus 210 may be quickly performed during startup or verification of the flow metering device 140.

The exhaust from the pressure chamber 214 may occur from the vent automatically or under control. In an example, the vent may be a size-restricted but uncontrolled orifice (e.g., an always-open pin-hole, of a fixed diameter) which allows venting from the gas verification apparatus 210 to an outside location such as the mixed gas line 150, a vacuum scavenging system, an open area of a housing or enclosure, ambient atmosphere, etc. To enable the measurement, one side of the exhaust provides a known pressure or, has predictable pressure. Here, use of outside pressure (e.g., outside of the chamber), can be easily utilized, since this provides consistent atmospheric pressure. In a varying example, the vent 216 may be a restricted and controlled orifice, which is actuated between an open state (e.g., openable to a consistent diameter or known size) or a closed state. The actuation of the vent 216 may occur based on the pressure sensor 218, the safety control 260, or other circuitry or components of the gas verification apparatus 210, flow metering device 140, or other control systems discussed herein.

In an example, the verification operations can be performed by the gas verification apparatus 210 upon startup of the flow metering device 140, prior to dispensing of gas to a patient. In other examples, verification operations by the gas verification apparatus 210 are performed as part of a testing or verification phase which may be automatically or manually initiated (e.g., by a user in a testing scenario, on a scheduled basis, etc.). The timing and number of the verification operations, involving pressure testing of the gases, may vary depending on implementations or type of uses, the type of gases, the usage of the flow metering device, or other factors.

In a further example, separate pressure chambers (e.g., two chambers) may be used for conducing the gas measurements and comparisons discussed herein. For instance, a separate chamber may be used for receiving and measuring the leak rate of each gas, provided that the chambers are include the same characteristics (e.g., if the volume of each chamber and the exhaust port of each chamber are identical or within some tolerance).

Figure 3:
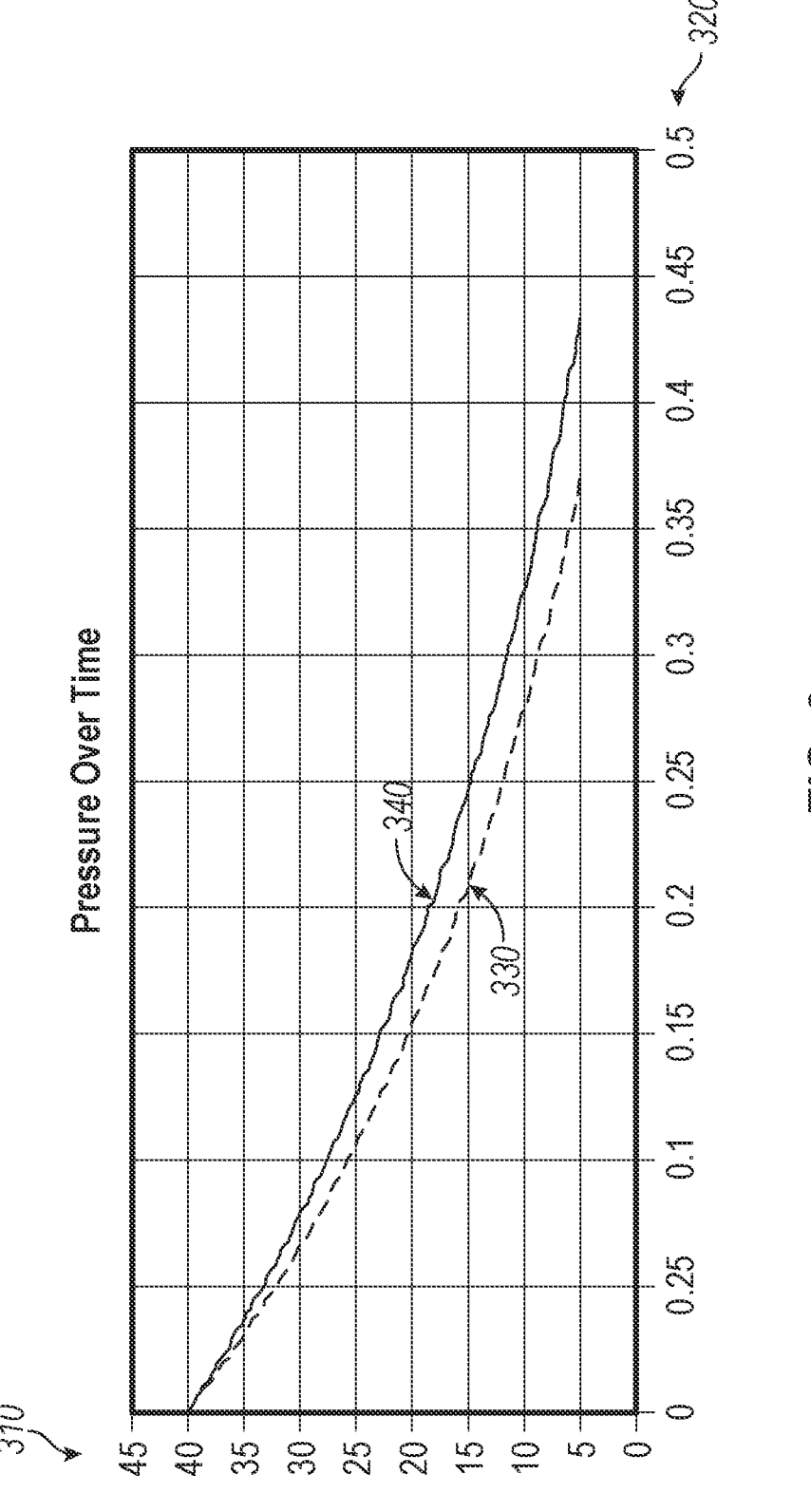
FIG. 3 includes a graphical illustration of pressure readings over time for anesthesia gases, according to an example.

FIG. 3 provides a graphical illustration of pressure readings over time for anesthesia gases, performed with a controlled leak sequence in a gas verification apparatus. The y-axis 310 depicts gas pressure of the chamber in psi gauge, and the x-axis 320 depicts time in seconds. The graph depicted in FIG. 3 indicates example measurements of chamber gas pressure over time, for a first gas 340, and a second gas 330, based on controlled exhaust from a pressure chamber (e.g., exhaust from the chamber 214 via the vent 216). In this illustrated example, the first gas 340 is pure nitrous oxide gas, and the second gas 330 is pure oxygen gas.

The time and pressure measurements indicated in FIG. 3 may reach thresholds (such as maximum and minimum values) to trigger the start and end of the pressure measurement. Gas that is typically supplied in anesthesia settings is provided from about 50 psi to about 60 psi gauge. As a result, the verification process may be configured to start time measurements for the leak rate from a defined start ("begin") pressure at a value less than the gas line pressure, such as at about 40 psi, or defined within the range of about 35 psi to about 45 psi gauge). Likewise, the end of the time measurements may coincide to reaching a defined concluding ("end") pressure that is at 0 psi or some greater value, such as defined with the range of about 5 psi to about 10 psi gauge. Other pressure values may be selected or calculated; further, the use of sensitive sensors may enable the use of smaller exhaust ranges in a shorter period of time.

A comparison of the amount of time needed to exhaust each gas from the begin pressure to the end pressure may indicate a variety of conditions. For example, an amount of time to exhaust a gas received from an input line expected to be oxygen, which is shorter than an amount of time to exhaust a gas received from an input line expected to be nitrous oxide, can indicate that no crossover is present. Conversely, a longer amount of time to exhaust a gas received from an input line expected to provide oxygen, than from an input line expected to provide nitrous oxide, may indicate that crossover is present. A same amount of time to exhaust gases from different input channels may indicate that the same type of gas is present in both input channels.

In other examples, a comparison of other pressure or time-based values or derivatives may be performed. For example, a microprocessor may compare the exhaust times between the begin and end pressures for two gases based on an expected (e.g., predetermined) ratio between the gases. In an example that uses an orifice to leak gas, the volumetric gas flow is proportional to the reciprocal of the square root of the gas mass density, and thus each of the gases will leak through the orifice at a different rate. Sizing the orifice sufficiently to keep complicating factors out of consideration, the ratio of leak rates between nitrous oxide and oxygen may be expected to be at or near a fixed value as shown by Equation (1) below:

$$\text{Leak ratio}_{(N_2O:O_2)} \cong \sqrt[2]{\frac{1.977 \text{ g/l}}{1.429 \text{ g/l}}} \cong 1.176 \tag{1}$$

Other types of comparisons, verifications, and actions may occur as part of gas line monitoring scenarios which involve time and pressure measurements from a controlled leak or exhaust.

FIG. 4 provides a flowchart 400 depicting a method of verifying and controlling gas delivery for anesthesia gases. The flowchart 400 provides a more detailed breakout of operations for measuring and verifying gas composition, such as with a sequential gas leak measurement performed with use of the chamber 214, vent 216, and pressure sensor 218, discussed above. However, it will be understood that the operations of 400 may also be modified for concurrent or simultaneous use of the gas measurements using dual chambers, vents, and sensors.

The operations of the flowchart 400 may be implemented based on electronically or electromechanically controlled actions, performed by the flow metering device 140, gas verification apparatus 210, or other devices or components discussed herein. However, it will be understood that external control from users or other external systems or entities may cause or control the operations of the flowchart 400.

The flowchart 400 includes a first cycle, involving the filling of a measurement chamber with a first gas to a determined chamber pressure (operation 401), followed by a measuring of the release (exhaust) of the first gas via a vent (operation 402, e.g., with vent 216). The measuring of the release of the first gas is based on chamber pressure readings from a pressure sensor (e.g., pressure sensor 218). One or more time measurements may be obtained based on the release, such as a total elapsed time to exhaust the first gas.

The flowchart 400 continues with a second cycle, similarly involving the filling of the measurement chamber with a second gas to the determined chamber pressure (operation 403, e.g., with the same chamber pressure used during the first cycle), followed by the measuring of the release (exhaust) of the first gas via the vent (operation 404, e.g., with vent 216). Again, the measuring of the release of the first gas is based on chamber pressure readings from the pressure sensor (e.g., pressure sensor 218), although a different or alternative pressure sensor or measurement technique may be used. One or more time measurements may be obtained based on the release, such as a total elapsed time to exhaust the second gas.

The flowchart 400 continues with an analysis cycle. This may include comparison of time measurements (operation 405), to compare the amount of time needed to release the first gas versus to the second gas, such as based on a total elapsed time reach an exhausted (end) pressure from a filled (begin) pressure in the chamber. This comparison is analyzed to identify one or more conditions of the input gases or equipment configurations (operation 406), based on the time measurement condition.

The flowchart 400, in some examples, may also include operations to control the gas delivery based on the one or more identified conditions (operation 407). For example, this may include the output of an alarm or status indicator, via an audible or visible indication. In further examples, the control operations may coordinate with other alarms or controls provided by failsafe devices (such as failsafe devices which activate when oxygen pressure falls below a defined psi or flow rate). In other examples, a failsafe device utilizing the gas flow principles previously described may be added onto a mechanical system in which case this failsafe device could have valves that would shut if the gases were mixed. In addition, this failsafe device could send out an alarm from its own speaker to alert the user that a problem was encountered. This would allow a failsafe device to control gases in a mechanical flowmeter.

Figure 5:
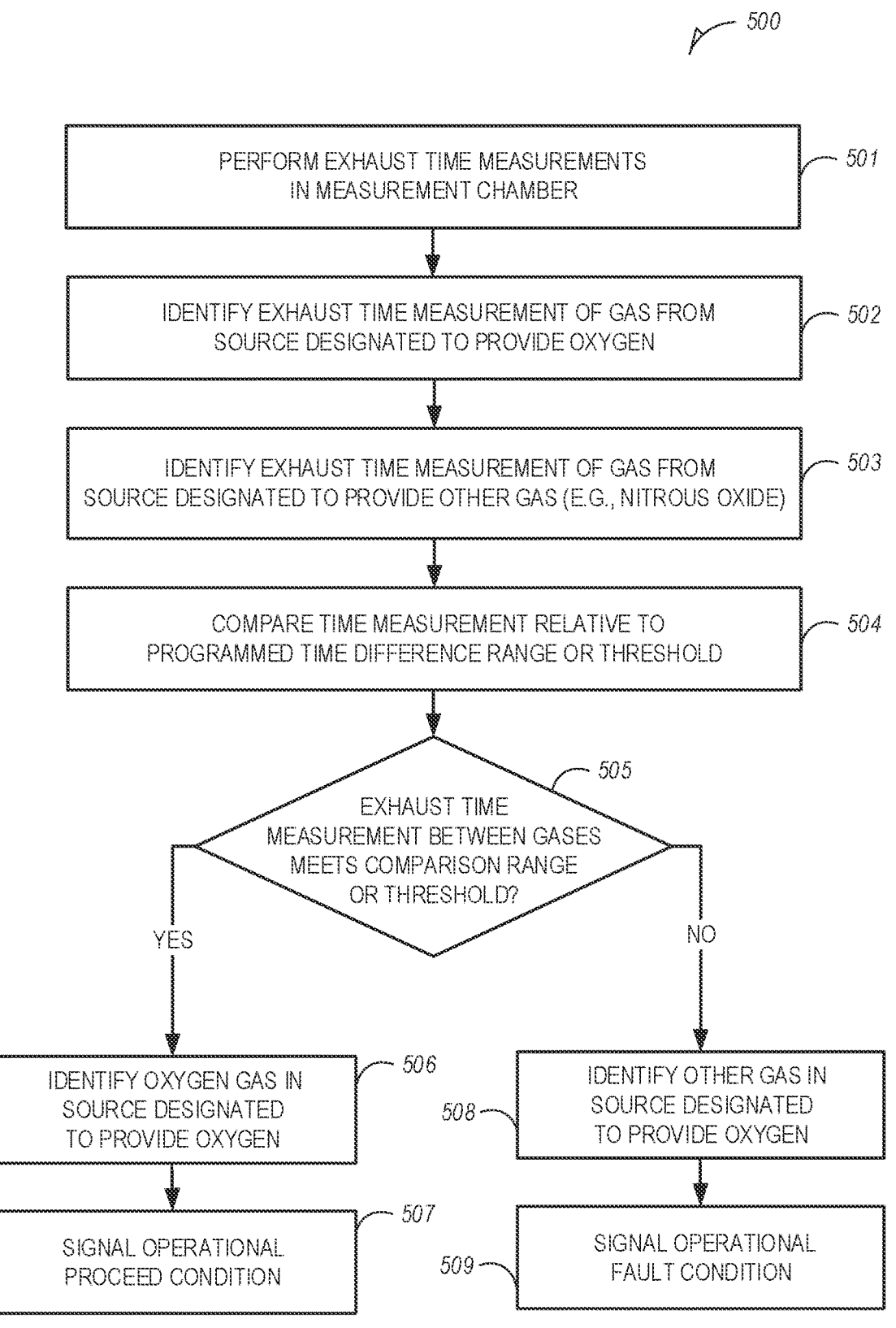
FIG. 5 includes a flowchart depicting a further method of identifying anesthesia gases and controlling operational conditions based on time measurements of exhausting the anesthesia gases, according to an example.

FIG. 5 provides a flowchart 500 depicting a further method of identifying anesthesia gases and controlling operational conditions based on time measurements of exhausting the anesthesia gases. This flowchart 500 may provide further verification operations that are implemented as part of or in substitute for operations 405-407, discussed above, or as standalone analysis operations (e.g., by a flowmeter safety control).

The flowchart 500 includes an operation to perform exhaust time measurements on one or more gases using a measurement chamber (operation 501), such as with the gas verification apparatus 210 discussed above. The results of these exhaust time measurements may provide values similar to those depicted in FIG. 3 above.

The flowchart 500 continues with the identification of a measurement(s) received from a source designated to provide oxygen gas (operation 502), and the identification of the measurement(s) received from a source designated to provide another gas (operation 503) such as nitrous oxide. The identification of these measurements may be based on time and pressure sensor data, for example, to produce a time measurement such as a total elapsed time for the respective gases.

The flowchart 500 continues with a comparison of the time measurements (operation 504), relative to a programmed time difference such as an expected leak rate for one or both gases, a ratio of leak rates between the gases, a threshold or range of time differences, or similar value comparisons. A determination is then performed to identify whether the exhaust time measurement between the gases meets the comparison range or threshold (decision 505). In the event that only one gas is being analyzed, operations 503-505 may be omitted or modified to perform a comparison of time and pressure values against a set of predetermined values (e.g., values which are specific to oxygen).

In response to a determination that the exhaust time satisfies the comparison range or threshold to identify oxygen (e.g., meets or exceeds the ratio, or has a different elapsed time for exhaust than the other gas), oxygen gas can be identified from the source designated to provide oxygen (operation 506). This can be accompanied by a signal of an operational proceed condition (operation 507, e.g., a "pass" for a gas verification test).

In response to a determination that the exhaust time does not satisfy the comparison range or threshold to identify oxygen (e.g., meets or exceeds the ratio, or does not have a different elapsed time for exhaust than the other gas), a non-oxygen gas can be identified from the source designated to provide oxygen (operation 508). This can be accompanied by a signal of an operational fault condition (operation 509, e.g., a "fail" for the gas verification test).

Figure 6:
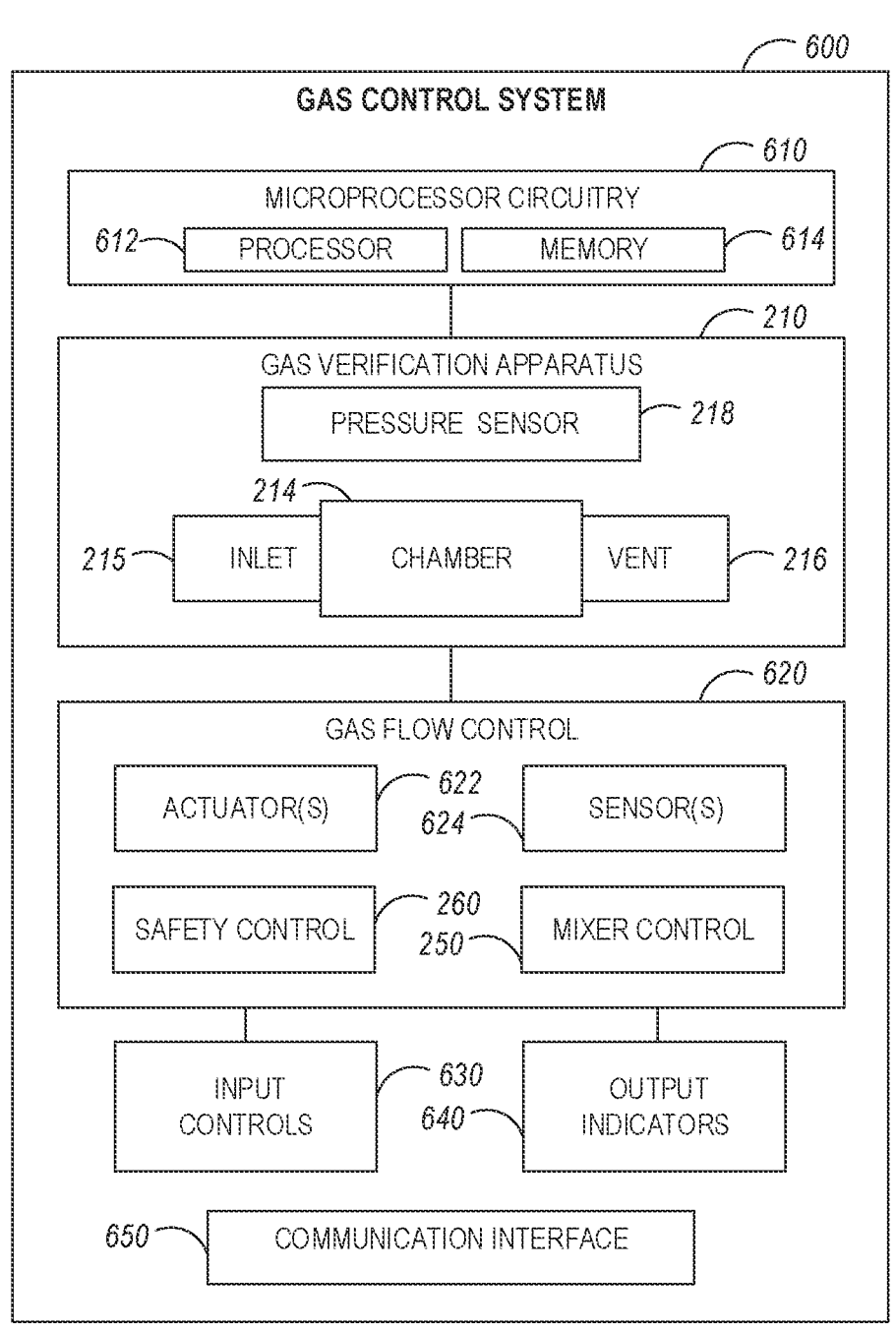
FIG. 6 is a block diagram of a gas control system, including a gas verification apparatus and gas flow control, according to an example.

FIG. 6 provides a block diagram of a gas control system 600, including the gas verification apparatus 210 and a gas flow control 620 configured for implementing techniques and methods discussed above. In various examples, the gas control system 600 may comprise a flowmeter, manifold, control system, or other gas control component.

The gas verification apparatus 210 may include the chamber 214 for receiving and measuring gas leak rates, through gas received via the inlet 215, exhausted with the vent 216, and measured with the pressure sensor 218, as discussed for FIG. 2 above. The gas verification apparatus 210 may include or be operably coupled to microprocessor circuitry 610 to allow the execution of instructions, programmed logic, or other forms of programming to accomplish digital processing and operations. The microprocessor circuitry 610 may include a processor 612, such as provided by a microprocessor, central processing unit (CPU), system-on-chip, or other processing circuitry, and a memory 614, such as provided by read only memory, random access memory, non-volatile storage memory, among other types of memory units. Various values, measurements, and information associated with the verification process or the gas control system generally may be maintained in the memory 614 and computed with the processor 612.

The gas flow control 620 may operate with the functionality or capabilities provided by the flow metering device 140, as discussed in the figures above; in the example of FIG. 6, the gas flow control 620 includes the safety control 260 and mixer control 250, in addition to one or more actuators 622 and one or more sensors 624. For instance, the one or more actuators 622 may control valves and outputs for mixing gas, based on signals from the mixer control 250. The one or more sensors 624 may observe and sense system states and gas flow conditions, and be used in operation of the safety control 260 and the mixer control 250.

The gas control system 600 may include input controls 630 used to operate the mixer control 250 and other features of the gas flow control 620, and output indicators 640 used to indicate a status of the mixer control 250 and other features of the gas flow control 620. For example, the input controls 630 may receive values for an input gas mixture, from a user, to mix multiple gases, which cause the actuators 622 and sensors 624 of the gas flow control 620 to mix and deliver gas via the mixer control 250 according to particular rates, ratios, or amounts. Likewise, the output indicators 640 may provide a user with a status of operation, based on the state of the actuators 622 and sensors of the gas flow control 620, according to the operation of the mixer control 250. The input controls 630 and output indicators 640 may also be involved with the use of the safety control 260, including with operation of safety operations provided by the gas verification apparatus 210.

The gas control system 600 may include a communication interface 650, used in connection with monitoring, verification, logging, or other operations. The gas control system 600 may also be operably or communicatively coupled to other gas delivery or distribution equipment, causing a shutdown or change in other equipment as a result of detected or identified conditions.

Although many of the previous examples are provided with reference to the measurement and verification of a first gas relative to a second gas, it will be understood that many of these procedures may be accomplished with evaluation or verification of a single gas, more than two gases, or adapted to other types of gas verification settings. For instance, a comparison of an elapsed exhaust time for gas received from an oxygen gas line may be compared to a recorded range of values, based on pre-calibrated or pre-determined oxygen gas values. Further, although many of the previous examples are provided with reference to use of oxygen and nitrous oxide gases, the present techniques and configurations can be used to differentiate between any two gases as long as they are sufficiently apart in density such that a sensor configuration can detect a meaningful difference in flow rates over a controlled pressure drop.

Additionally, although many of the previous examples are provided with reference to the integration of the gas verification apparatus within a flowmeter, the gas verification apparatus may be hosted as a standalone, add-on unit that is attachable/couplable to an exterior of a flowmeter, manifold, or other gas distribution equipment. It will also be understood the various safety alarms, sensors, actuators, may be controlled or provided by a standalone or separate device, such as with the use of a valve actuator which restricts or shuts off a port or a gas source in response to detecting an unexpected condition. The gas verification apparatus may also provide remote control and monitoring features, such as to receive or send a restriction or shutoff command to connected gas distribution equipment in response to detecting an unexpected condition. Other use cases and variations may also be provided with use of the present verification systems and methods in a gas verification apparatus and flowmeter equipment.

VARIOUS NOTES & EXAMPLES

Each of these non-limiting examples can stand on its own, or can be combined in various permutations or combinations with one or more of the other examples.

Example 1 is an apparatus for verifying input gases, the apparatus comprising: a chamber adapted to receive a gas, the chamber including: an inlet to receive the gas; and a vent to exhaust the gas; a pressure sensor arranged to measure pressure within the chamber; a gas control coupled to the inlet, the gas control configured to fill a first gas and a second gas into the chamber at respective times, the gas control operable to: fill the chamber with the first gas to a defined begin pressure; and fill the chamber with the second gas to the defined begin pressure; and microprocessor circuitry, coupled to the pressure sensor, the microprocessor circuitry operable to: observe pressure in the chamber at a first time period, measured with the pressure sensor, to identify a first elapsed time to exhaust the first gas from the chamber, via the vent, and reach a defined end pressure; observe pressure in the chamber at a second time period, measured with the pressure sensor, to identify a second elapsed time to exhaust the second gas from the chamber, via the vent, and reach the defined end pressure; and identify a difference between the first gas and the second gas, based on a time difference between the first elapsed time and the second elapsed time.

In Example 2, the subject matter of Example 1 includes, an example where one of the first and second gas is oxygen gas and wherein the other of the first and second gas is nitrous oxide gas, and wherein the inlet is connected to an intake designated to receive the oxygen gas and an intake designated to receive the nitrous oxide gas.

In Example 3, the subject matter of Example 2 includes, the microprocessor circuitry further operable to: identify receipt of the oxygen gas from the intake designated to receive the oxygen gas and identify receipt of the nitrous oxide gas from the intake designated to receive the nitrous oxide gas, in response to: (i) the elapsed time to reach the defined end pressure by exhaust of gas received from the intake designated to receive the nitrous oxide gas exceeding (ii) the elapsed time to reach the defined end pressure by exhaust of gas received from the intake designated to receive the oxygen gas.

In Example 4, the subject matter of Example 3 includes, the microprocessor circuitry further operable to: output a signal to the gas control, in response to identifying receipt of the oxygen gas from the intake designated to receive the oxygen gas and identifying receipt of the nitrous oxide gas from the intake designated to receive the nitrous oxide gas.

In Example 5, the subject matter of Examples 2-4 includes, the microprocessor circuitry further operable to: identify receipt of an improper gas from the intake designated to receive the oxygen gas or identify receipt of an improper gas from the intake designated to receive the nitrous oxide gas, in response to: (i) the elapsed time to reach the defined end pressure by exhaust of gas received from the intake designated to receive the nitrous oxide gas not exceeding (ii) the elapsed time to reach the defined end pressure by exhaust of gas received from the intake designated to receive the oxygen gas.

In Example 6, the subject matter of Examples 1-5 includes, the microprocessor circuitry further configured to: signal an operational proceed condition in response to the time difference between the first elapsed time and the second elapsed time being within a defined range; and signal an operational fault condition in response to the time difference between the first elapsed time and the second elapsed time not being within the defined range; wherein the signal of the operational proceed condition or the signal of the operational fault condition causes a control of gas flow for one or both of the first and second gas.

In Example 7, the subject matter of Examples 1-6 includes, the microprocessor circuitry operably coupled to a gas flow meter, wherein operation of the gas flow meter for dispensing of the first gas and the second gas occurs in response to identifying a difference between the first gas relative to the second gas.

In Example 8, the subject matter of Example 7 includes, an example where the gas flow meter is a mechanical flow meter, and wherein the operation of the mechanical flow meter is controlled to actuate at least one gas flow valve.

In Example 9, the subject matter of Examples 7-8 includes, an example where the gas flow meter is a digital flow meter, wherein the microprocessor circuitry is operable to provide a signal to control the operation of the digital flow meter.

In Example 10, the subject matter of Examples 1-9 includes, an example where the vent is an orifice that provides an opening of a fixed diameter for exhaust of the first gas and the second gas from the chamber.

In Example 11, the subject matter of Examples 1-10 includes, an example where the vent is arranged to exhaust the gas to: a mixed gas line, a scavenging vacuum line, or atmosphere.

In Example 12, the subject matter of Examples 1-11 includes, an example where the defined end pressure is within a range of 5 and 10 psi gauge, and wherein the defined begin pressure is within a range of 35 and 45 psi gauge.

In Example 13, the subject matter of Examples 1-12 includes, an example where the chamber comprises a first chamber to receive and exhaust the first gas, and a second chamber to receive and exhaust the second gas, and wherein the pressure sensor comprises a first pressure sensor to measure the pressure within the first chamber and a second pressure chamber to measure the pressure within the second chamber.

Example 14 is a gas flow control system, comprising: a first intake adapted to receive a first gas and a second intake adapted to receive a second gas, wherein one of the first and second intake is designated to receive oxygen gas, and wherein the other of the first and second intake is designated to receive nitrous oxide gas; a chamber, the chamber including an inlet to receive gas and a vent to exhaust the gas, the inlet connected to the first intake and the second intake; and a gas control coupled to the chamber, the gas control operable to respectively fill the chamber with the first gas and fill the chamber with the second gas to a determined begin pressure; a microprocessor configured to measure respective times to exhaust the first gas and the second gas from the chamber, via the vent, and reach a determined end pressure; and wherein the gas control is configured to enable gas flow for the first gas and the second gas, in response to a time to exhaust a gas received from the intake designated to receive the nitrous oxide gas exceeding the time to exhaust a gas received from the intake designated to receive the oxygen gas.

In Example 15, the subject matter of Example 14 includes, an example where the gas control is configured to restrict gas flow for one or both of the first and second gas, in response to the time to exhaust the gas received from the intake designated to receive the nitrous oxide gas not exceeding the time to exhaust the gas received from the intake designated to receive the oxygen gas.

In Example 16, the subject matter of Example 15 includes, a gas mixer to control a rate of gas to output, combined from the first and second gas received from the first and second intakes, according to a designated mix of the oxygen gas and the nitrous oxide gas.

In Example 17, the subject matter of Examples 14-16 includes, an example where the vent is an orifice that provides an opening of a fixed diameter for exhaust of the first gas and the second gas from the chamber.

In Example 18, the subject matter of Examples 14-17 includes, an example where the vent is arranged to exhaust the gas to: a mixed gas line, a scavenging vacuum line, or atmosphere.

In Example 19, the subject matter of Examples 14-18 includes, an example where the determined end pressure is within a range of 5 and 10 psi gauge, and wherein the determined begin pressure is within a range of 35 and 45 psi gauge.

Example 20 is a method of verifying input gases, the method comprising: filling a chamber with a first gas to a defined begin pressure, at a first time period, based on receipt of the first gas from a first inlet, wherein the chamber includes, a vent therein; monitoring pressure in the chamber during the first time period, using a pressure sensor, to measure a first time to exhaust the first gas from the chamber, via the vent, to reach a defined end pressure; filling the chamber with a second gas to the defined begin pressure, at a second time period, based on receipt of the second gas from a second inlet; monitoring pressure in the chamber during the second time period, using the pressure sensor, to measure a second time to exhaust the second gas from the chamber, via the vent, to reach the defined end pressure; and identifying a difference between the first and second gas, based on a difference between the first time and the second time.

In Example 21, the subject matter of Example 20 includes, wherein identifying a difference between the first and second gas includes identifying one of the first and second gas as oxygen, and the other of the first and second gas as nitrous oxide, in response to the time to reach the defined end pressure by exhaust of the nitrous oxide gas exceeding the time to reach the defined end pressure by exhaust of the oxygen gas.

In Example 22, the subject matter of Example 21 includes, determining whether the one of the first and second gas identified as oxygen is connected to the one of the first and second inlets which is designated for oxygen, and the other of the first and second gas identified as nitrous oxide is connected to the other of the first and second inlets which is designated for nitrous oxide; identifying an error condition based on determining either that: a gas not identified as oxygen is received in the one of the first and second inlets which is designated for oxygen; or a gas not identified as nitrous oxide is received in the other of the first and second inlets which is designated for nitrous oxide.

In Example 23, the subject matter of Example 22 includes, outputting an alert based on identifying the error condition.

In Example 24, the subject matter of Examples 22-23 includes, an example where the method is performed by a component of a gas flow control system, the method further comprising: controlling flow of the first gas and the second gas, with the gas flow control system, based on identifying the error condition.

In Example 25, the subject matter of Examples 20-24 includes, an example where the defined end pressure is within a range of 5 and 10 psi gauge, and wherein the defined begin pressure is within a range of 35 and 45 psi gauge.

Example 26 is at least one machine-readable medium including instructions that, when executed by circuitry, cause the circuitry to perform operations to implement of any of Examples 1-25.

Example 27 is an apparatus comprising respective means to implement of any of Examples 1-25.

Example 28 is a system to implement of any of Examples 1-25.

Example 29 is a method to implement of any of Examples 1-25.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device (including processing circuitry within such electronic device) to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The following claims are hereby incorporated into the Detailed Description as examples or embodiments, with each claim standing on its own as a separate embodiment, and it is contemplated that such embodiments can be combined with each other in various combinations or permutations.

What is claimed is:

1. An apparatus for verifying input gases, the apparatus comprising:
   a chamber adapted to receive a gas, the chamber including:
      an inlet to receive the gas; and
      a vent to exhaust the gas;
   a pressure sensor arranged to measure pressure within the chamber;
   a gas control coupled to the inlet, the gas control configured to fill a first gas and a second gas into the chamber at respective times, the gas control operable to:
      fill the chamber with the first gas to a defined begin pressure; and
      fill the chamber with the second gas to the defined begin pressure; and
   microprocessor circuitry, coupled to the pressure sensor, the microprocessor circuitry operable to:
      observe pressure in the chamber at a first time period, measured with the pressure sensor, to identify a first elapsed time to exhaust the first gas from the chamber, via the vent, and reach a defined end pressure;
      observe pressure in the chamber at a second time period, measured with the pressure sensor, to identify a second elapsed time to exhaust the second gas from the chamber, via the vent, and reach the defined end pressure; and
      identify a difference between the first gas and the second gas, based on a time difference between the first elapsed time and the second elapsed time
      wherein one of the first and second gas is oxygen gas and wherein the other of the first and second gas is nitrous oxide gas, and wherein the inlet is connected to a first intake designated to receive the oxygen gas and a second intake designated to receive the nitrous oxide gas.

2. The apparatus of claim 1, the microprocessor circuitry further operable to:
   identify receipt of the oxygen gas from the intake designated to receive the oxygen gas and identify receipt of the nitrous oxide gas from the intake designated to receive the nitrous oxide gas, in response to
      one of the first elapsed time or the second elapsed time to reach the defined end pressure by exhaust of gas received from the intake designed to receive the nitrous oxide gas exceeding the other of the first elapsed time or the second elapsed time to reach the defined end pressure by exhaust of gas received from the intake designed to receive the oxygen gas.

3. The apparatus of claim 2, the microprocessor circuitry further operable to:
   output a signal to the gas control, in response to identifying receipt of the oxygen gas from the intake designated to receive the oxygen gas and identifying receipt of the nitrous oxide gas from the intake designated to receive the nitrous oxide gas.

4. The apparatus of claim 1, the microprocessor circuitry further operable to:

identify receipt of an improper gas from the intake designated to receive the oxygen gas or identify receipt of an improper gas from the intake designated to receive the nitrous oxide gas, in response to one of the first elapsed time or the second elapsed time to reach the defined end pressure by exhaust of gas received from the intake designed to receive the nitrous oxide gas not exceeding the other of the first elapsed time or the second elapsed time to reach the defined end pressure by exhaust of gas received from the intake designed to receive the oxygen gas.

5. The apparatus of claim 1, the microprocessor circuitry further configured to:

signal an operational proceed condition in response to the time difference between the first elapsed time and the second elapsed time being within a defined range; and signal an operational fault condition in response to the time difference between the first elapsed time and the second elapsed time not being within the defined range;

wherein the signal of the operational proceed condition or the signal of the operational fault condition causes a control of gas flow for one or both of the first and second gas.

6. The apparatus of claim 1, the microprocessor circuitry operably coupled to a gas flow meter, wherein operation of the gas flow meter for dispensing of the first gas and the second gas occurs in response to identifying the difference between the first gas and the second gas.

7. The apparatus of claim 6, wherein the gas flow meter is a mechanical flow meter, and wherein the operation of the mechanical flow meter is controlled to actuate at least one gas flow valve.

8. The apparatus of claim 6, wherein the gas flow meter is a digital flow meter, wherein the microprocessor circuitry is operable to provide a signal to control an operation of the digital flow meter.

9. The apparatus of claim 1, wherein the vent is an orifice that provides an opening of a fixed diameter for exhaust of the first gas and the second gas from the chamber.

10. The apparatus of claim 1, wherein the vent is arranged to exhaust the gas to: a mixed gas line, a scavenging vacuum line, or atmosphere.

11. The apparatus of claim 1, wherein the defined end pressure is within a range of 5 and 10 psi gauge, and wherein the defined begin pressure is within a range of 35 and 45 psi gauge.

12. The apparatus of claim 1, wherein the chamber comprises a first chamber to receive and exhaust the first gas, and a second chamber to receive and exhaust the second gas, and wherein the pressure sensor comprises a first pressure sensor to measure the pressure within the first chamber and a second pressure chamber to measure the pressure within the second chamber.

13. A gas flow control system, comprising:

a first intake adapted to receive a first gas and a second intake adapted to receive a second gas, wherein one of the first and second intake is designated to receive oxygen gas, and wherein the other of the first and second intake is designated to receive nitrous oxide gas;

a chamber, the chamber including an inlet to receive gas and a vent to exhaust the gas, the inlet connected to the first intake and the second intake; and a gas control coupled to the chamber, the gas control operable to respectively fill the chamber with the first gas and fill the chamber with the second gas to a determined begin pressure;

a microprocessor configured to measure respective times to exhaust the first gas and the second gas from the chamber, via the vent, and reach a determined end pressure; and wherein the gas control is configured to enable gas flow for the first gas and the second gas, in response to a time to exhaust a gas received from the intake designated to receive the nitrous oxide gas exceeding the time to exhaust a gas received from the intake designated to receive the oxygen gas.

14. The gas flow control system of claim 13, wherein the gas control is configured to restrict gas flow for one or both of the first and second gas, in response to the time to exhaust the gas received from the intake designated to receive the nitrous oxide gas not exceeding the time to exhaust the gas received from the intake designated to receive the oxygen gas.

15. The gas flow control system of claim 14, further comprising:

a gas mixer to control a rate of gas to output, combined from the first and second gas received from the first and second intakes, according to a designated mix of the oxygen gas and the nitrous oxide gas.

16. The gas flow control system of claim 13, wherein the vent is an orifice that provides an opening of a fixed diameter for exhaust of the first gas and the second gas from the chamber.

17. The gas flow control system of claim 13, wherein the vent is arranged to exhaust the gas to: a mixed gas line, a scavenging vacuum line, or atmosphere.

18. The gas flow control system of claim 13, wherein the determined end pressure is within a range of 5 and 10 psi gauge, and wherein the determined begin pressure is within a range of 35 and 45 psi gauge.

* * * * *